(12) United States Patent
Hamm et al.

(10) Patent No.: US 10,952,702 B2
(45) Date of Patent: Mar. 23, 2021

(54) NON-UNIFORM ROTATIONAL DISTORTION DETECTION CATHETER SYSTEM

(71) Applicant: Canon U.S.A. Inc., Melville, NY (US)

(72) Inventors: Mark Alan Hamm, Lynnfield, MA (US); Bin Wu, West Roxbury, MA (US); Albert Dunfee, Newbury, MA (US); Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 530 days.

(21) Appl. No.: 15/628,093

(22) Filed: Jun. 20, 2017

(65) Prior Publication Data
US 2017/0360398 A1 Dec. 21, 2017

Related U.S. Application Data

(60) Provisional application No. 62/352,741, filed on Jun. 21, 2016.

(51) Int. Cl.
*A61B 8/12* (2006.01)
*A61B 8/00* (2006.01)
*G01S 7/52* (2006.01)
*G01S 15/89* (2006.01)

(52) U.S. Cl.
CPC .............. *A61B 8/4254* (2013.01); *A61B 8/12* (2013.01); *A61B 8/445* (2013.01); *G01S 7/5205* (2013.01); *G01S 15/894* (2013.01); *A61B 8/4461* (2013.01)

(58) Field of Classification Search
CPC ... A61B 18/1492; A61B 1/00096; A61B 1/05; A61B 2017/003; A61B 2090/364; A61M 2025/0681; A61M 25/0147
See application file for complete search history.

(56) References Cited

U.S. PATENT DOCUMENTS

| | | |
|---|---|---|
| 5,186,177 A | 2/1993 | O'Donnell et al. |
| 5,699,806 A | 12/1997 | Webb et al. |
| 5,760,306 A | 6/1998 | Wyatt, III et al. |
| 6,450,964 B1 | 9/2002 | Webler |
| 6,493,575 B1 | 12/2002 | Kesten et al. |
| 6,915,955 B2 | 7/2005 | Jung et al. |

(Continued)

FOREIGN PATENT DOCUMENTS

| | | |
|---|---|---|
| CN | 203732801 U | 7/2014 |
| WO | 2015111053 A1 | 7/2015 |

(Continued)

OTHER PUBLICATIONS

Wang et al., Heartbeat OCT: in vivo intravascular megahertz-optical coherence tomography, Nov. 2015 (Year: 2015).*

(Continued)

*Primary Examiner* — Boniface N Nganga
(74) *Attorney, Agent, or Firm* — Canon U.S.A., Inc. IP Division

(57) ABSTRACT

Exemplary probes including longitudinal marker elements arranged parallel to the probe axis are provided for reducing or eliminating non-uniform rotational distortions (NURD) in imaging systems. Additional ring marker elements may also be provided to reduce or eliminate non-uniform linear distortion (NULD). These probes, as well as systems and methods of use provide for images having better image quality and reduced NURD.

20 Claims, 9 Drawing Sheets

(56) References Cited

U.S. PATENT DOCUMENTS

| | | | |
|---|---|---|---|
| 7,024,025 | B2 | 4/2006 | Sathyanarayana |
| 7,044,004 | B2 | 5/2006 | Hurley et al. |
| 7,366,376 | B2 | 4/2008 | Shishkov et al. |
| 7,538,878 | B2 | 5/2009 | Jung et al. |
| 7,545,518 | B2 | 6/2009 | Heyworth |
| 7,637,870 | B2 | 12/2009 | Flaherty et al. |
| 7,843,572 | B2 | 11/2010 | Tearney et al. |
| 8,197,413 | B2 | 6/2012 | Kurse et al. |
| 8,928,889 | B2 | 1/2015 | Tearney et al. |
| 9,087,368 | B2 | 7/2015 | Tearney et al. |
| 9,332,942 | B2 | 5/2016 | Jaffer et al. |
| 9,557,154 | B2 | 1/2017 | Tearney et al. |
| 2003/0100869 | A1* | 5/2003 | Wang ............. A61M 25/0009 604/264 |
| 2009/0137876 | A1* | 5/2009 | Brophy ............. A61B 1/0615 600/167 |
| 2010/0092389 | A1 | 4/2010 | Jaffer et al. |
| 2011/0292400 | A1 | 12/2011 | Fleming et al. |
| 2012/0172698 | A1 | 7/2012 | Teo et al. |
| 2013/0204126 | A1* | 8/2013 | Namati ............. A61B 8/12 600/427 |
| 2013/0231558 | A1* | 9/2013 | Goodnow ............. A61B 8/12 600/425 |
| 2014/0018669 | A1 | 1/2014 | Xu |
| 2014/0228636 | A1* | 8/2014 | Nimkar ............. A61B 1/0005 600/109 |
| 2014/0323877 | A1 | 10/2014 | Courtney et al. |
| 2015/0297182 | A1* | 10/2015 | Peng ............. A61B 8/4281 600/467 |
| 2016/0242845 | A1 | 8/2016 | Matsui |
| 2017/0135584 | A1 | 5/2017 | Tearney et al. |
| 2017/0209049 | A1 | 7/2017 | Wang et al. |
| 2018/0064396 | A1 | 3/2018 | Wang |

FOREIGN PATENT DOCUMENTS

| | | | |
|---|---|---|---|
| WO | 2015/116939 A1 | 8/2015 | |
| WO | 2015/116951 A1 | 8/2015 | |
| WO | WO-2015168594 A9 * | 1/2016 | ............. A61B 5/07 |
| WO | 2017/024145 A1 | 2/2017 | |
| WO | 2017/024234 A1 | 2/2017 | |

OTHER PUBLICATIONS

Ahsen et al., Correction of rotational distortion for catheter-based en face OCT and OCT angiography, Oct. 2014 (Year: 2014).*

Kawase et al., Comparison of Nonuniform Rotational Distortion Between Mechanical IVUS and OCT Using a Phantom Model, 2007 (Year: 2007).*

Tsai et al.,"Ultrahigh speed endoscopic swept source optical coherence tomography using a VCSEL light source and micromotor catheter" Proc. SPIE 8927, Endoscopic Microscopy IX; and Optical Techniques in Pulmonary Medicine, 89270T (Mar. 4, 2014) (Year: 2014).*

Osman, O. et al., "Correction of rotational distortion for catheter-based en face OCT and OCT angiography", Opt Lett. Oct. 15, 2014, pp. 5973-5976, vol. 39, No. 20.

Van Soest, G. et al., "Alignment of intravascular optical coherence tomography movies affected by non-uniform rotation distortion", Proceedings of SPIE, Jan. 2008, vol. 6847.

Tabatabaei, N. et al., Tethered confocal endomicroscopy capsule for diagnosis and monitoring of eosinophillic esophagitis, Biomed Opt Express, Dec. 13, 2013, vol. 5, No. 1, pp. 197-207.

Sun, C. et al., "In vivo feasibility of endovascular Doppler optical coherence tomography", Biomedical Optics Express, Oct. 1, 2012, pp. 2600-2610, vol. 3, No. 1.

Cho, H.S., et al, "High frame-rate intravascular optical frequency-domain imaging in vivo" Biomed Opt Express, Jan. 1, 2014, pp. 223-232, vol. 5, No. 1.

* cited by examiner

NON-UNIFORM ROTATIONAL DISTORTION DETECTION CATHETER SYSTEM

CROSS-REFERENCE TO RELATED APPLICATION(S)

This application claims priority to U.S. Provisional Application Ser. No. 62/352,741 filed 21 Jun. 2016, the content of which is incorporated herein by reference in its entirety.

FIELD OF THE DISCLOSURE

The present disclosure relates to imaging catheters. More particularly, the disclosure exemplifies imaging catheters that have reduced non-uniform image distortion.

BACKGROUND INFORMATION

Non-Uniform Rotational Distortion (NURD) is a well-known imaging artifact that occurs in catheter-based imaging systems caused by imperfect performance of the drive cable, the component that is responsible for keeping the distal imaging optics at the identical angular position as the motor. When the drive cable does not perfectly translate this angular position, rather storing and releasing energy due to asymmetry, frictional or tortuous path conditions, NURD is created. This stretches portions of the single-frame image and compresses other portions creating image artifacts that could have serious implications and results due to in-accurate information perceived by the clinician.

NURD artifacts are common in imaging catheters that employ flexible drive shafts to rotate the imaging elements at the distal end of the device. Common conception is that it is never completely eliminated. However, as long as the extent of NURD is small enough not to be noticed by the user and does not distort on-screen measurements, it is not considered a problem. The occurrence and severity of NURD is generally relative to the tortuosity of the path in which the catheter is positioned, and is a dynamic rather than stable phenomenon.

Another type of image distortion can occur when drive cable stretches during imaging pull-back called Non-Uniform Linear Distortion (NULD). This type of distortion can also be minimally problematic. However, when significant stretching occurs, NULD can mislead clinicians with serious consequences.

Thus, it is important to reduce or eliminate NURD and, when applicable, NULD.

One way of eliminating NURD is to position an encoder at the distal end of the imaging device, and another proposed method utilizes a varying wall thickness imaging window to indicate where the distal optics are pointed. Another method is to use geometric structures such as deployed stent struts, measuring the gaps between struts, relative distance or time elapsed between struts to detect NURD. However, coronary catheters are too small to effectively employ an encoder at the distal tip (see, in contrast, (U.S. Pat. Pub. 2014/0323877). Additionally, the cost and complexity of each of these methods, particularly when using a coronary catheter, may preclude their use in some products, and the fact that the product is for use inside the coronary and for particularly imaging modalities (e.g., OCT) will preclude the use of other products. For example, the variable wall thickness (see U.S. Pat. No. 6,450,964) will cause variable optical properties, which present problems for accurate OCT imaging and also yields variable catheter stiffness in different angular directions depending on wall thickness. The measurement of the spacing of stent struts during imaging (U.S. Pat. Pub. 2014/0018669) cannot be used for images prior to stent placement, and also depends of proper deployment and angular distribution of the stent struts, which is not guaranteed. Additionally, this method would presumably be accurate only when the catheter is centrally located in the vessel, because spacing appears uneven if the catheter is not located in the center of the vessel.

Thus, there is need for a coronary catheter with a method of reducing or preventing NURD that is applicable in small catheters such as coronary catheters.

SUMMARY OF EXEMPLARY EMBODIMENTS

According to at least one embodiment of the invention, there is provided a probe comprising: a rotatable imaging core comprising an imaging component and having a rotational axis; a cylindrical tube surrounding the imaging core, having the same rotational axis and having a proximal end, a distal end, and a lumen extending therebetween, the distal end of the cylindrical tube comprising: an imaging window, and a plurality of longitudinal marker elements, which are arranged parallel to the rotational axis and which may be equally spaced, integral with or attached to the imaging window. The plurality of marker elements do not substantially interfere with imaging detector performance. In some embodiments, the plurality of marker elements are not detected by a detector element when the detector element is detecting an image generated by the imaging core. The marker elements may be configured and adapted for detecting NURD.

There is also provided herein an imaging catheter system comprising a probe as described herein, optical fibers, a patient interface unit connected to the proximal end of the cylindrical tube (e.g., the catheter sheath), at least one detector, and an imaging console connected to the patient interface unit.

In some embodiments, the plurality of longitudinal marker elements form longitudinal stripes (e.g., at least 2, 4, 6, 8, or more) on the imaging window. They may be located at equal angular intervals around the imaging window. They may be thin strips as compared to the circumference of the cylindrical tube; for example, they may each be less than 15°, or less than 10° or less than 1° in width. The plurality of longitudinal marker elements may be, for example, light-scattering marker elements and/or fluorescent marker elements. They all may be the same, or they may be different. They may, for example, comprise the same material as the imaging window and a dopant material. In other embodiments, they are formed from a different material.

In some embodiments, the probe also includes a plurality of marker rings arranged circumferentially and that are substantially equally spaced along the imaging window. These marker rings may be configured and adapted for detecting NULD.

The probe may be adapted or configured for forming an image of an in vivo sample. For example, the probe may be used for imaging the coronary vasculature and may be configured for both rotation and for linear pull-back. The probe may be, for example, an optical coherence tomography (OCT) probe or a spectrally encoded endoscopic (SEE) probe. Similarly, the probe may be equipped with forward and/or side-viewing capabilities. If forward-looking, imaging may utilize marker elements on the imaging window, arranged in an equally spaced, radial pattern so the illumination beam scans by the marker elements as it images in the forward direction.

The imaging console may be configured to form 3-dimensional images. These images can be corrected for NURD. In particular, the detector may be configured or adapted to detect the apparent rotation angle of the plurality of longitudinal marker elements to each other. This detector may be the same or different as the detector used to detect the image.

A method is provided herein for monitoring non-uniform rotational distortion (NURD) comprising:

(a) rotating the imaging core of probe, where the probe comprises: the rotatable imaging core comprising an imaging component and having a rotational axis; a cylindrical tube surrounding the imaging core, having the same rotational axis and having a proximal end, a distal end, and a lumen extending therebetween, the distal end of the cylindrical tube comprising: an imaging window, and a plurality of longitudinal marker elements integral with or attached to the imaging window and arranged parallel to the rotational axis, (b) obtaining a raw image, (c) determining at least one of the apparent angular position of at least two of the plurality of longitudinal marker elements or the timing between signals from at least two of the plurality of longitudinal marker elements, and (d) computing the difference between the relative angular position and a theoretical angular position based on average rotational speed for the longitudinal marker elements.

In some embodiments, NURD is detected during pull-back of the imaging core. In other embodiments, NURD is detected prior to a pull-back.

In some embodiments, after the difference is computed, the raw image is corrected based on the computed difference. A message indicating the existence of NURD, the lack of NURD, or the amount of NURD may be displayed. The step of computing the difference may, for example, comprise forming an estimation matrix [A] based on the theoretical angular position of the longitudinal marker elements and comparing the detected angular position of the longitudinal marker elements with the theoretical angular position of said longitudinal marker elements. The step of correcting the raw image may comprise resampling A-lines to a uniform spacing.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

Figure 1:
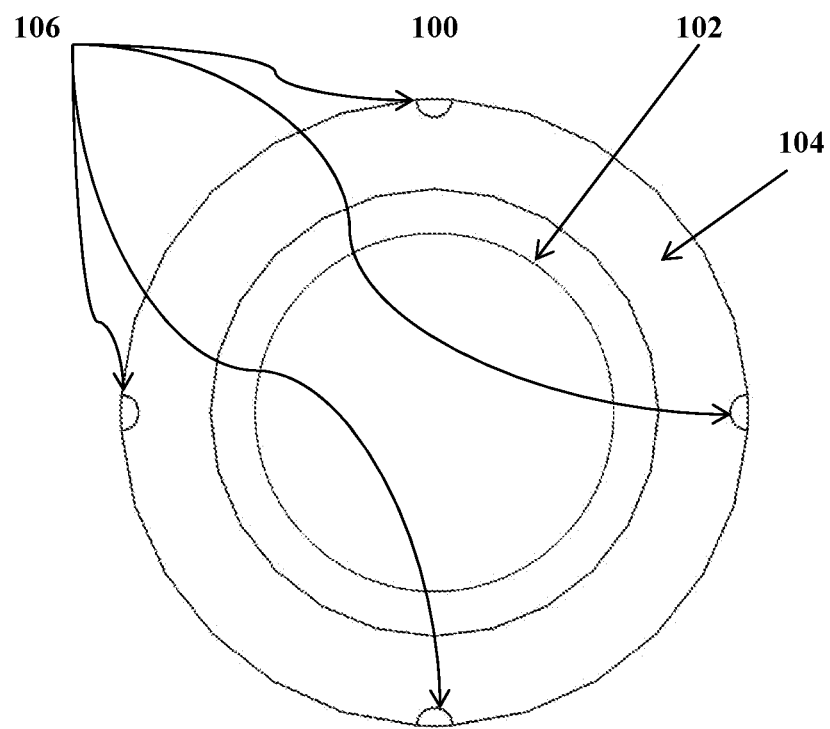
FIG. 1. Raw striped catheter imaging window extrusion, end view.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Thus, there is provided an apparatus and method for eliminating NURD. This is particularly useful for eliminating NURD in a small diameter catheter such as a coronary OCT or IVUS catheter.

The invention is particularly advantageous since it utilizes the existing imaging system to detect and count time intervals between fluorescent or scattering marker elements that are located in or on the outer surface of the imaging window comprising a cylindrical polymer tube. The marker elements are located at regular angular intervals around the cylindrical tube (e.g. at the periphery of the outer wall), and are detectable using the imaging system of the device without significantly interfering with optical imaging of the anatomy. In some embodiments of forward-looking probes, marker elements are located in or on the imaging window, arranged in a radial pattern where the marker elements are equally spaced similar so that a certain frequency is generated as the system scans the marker elements. When detected time intervals of imaging the marker elements is not uniform and regular, NURD exists and the system can calculate and correct the angular position of those detected markers, and also with them the angular location of imaged anatomy, thus correcting the NURD.

In more detail, FIG. 1 shows a cross-sectional view of catheter probe 100 that depicts the imaging window portion of a cylindrical tube 104. At regular angular intervals around outer surface of the cylindrical tube 104, longitudinal marker elements 106 are found. The cylindrical tube 104 at the distal end comprises an imaging window through which an imaging assembly can form an image. The imaging assembly is contained in an imaging core 102 located inside cylindrical tube 104. Marker elements 106 may be located on the outer diameter, inner diameter, or within the wall of cylindrical tube 104.

Figure 2:
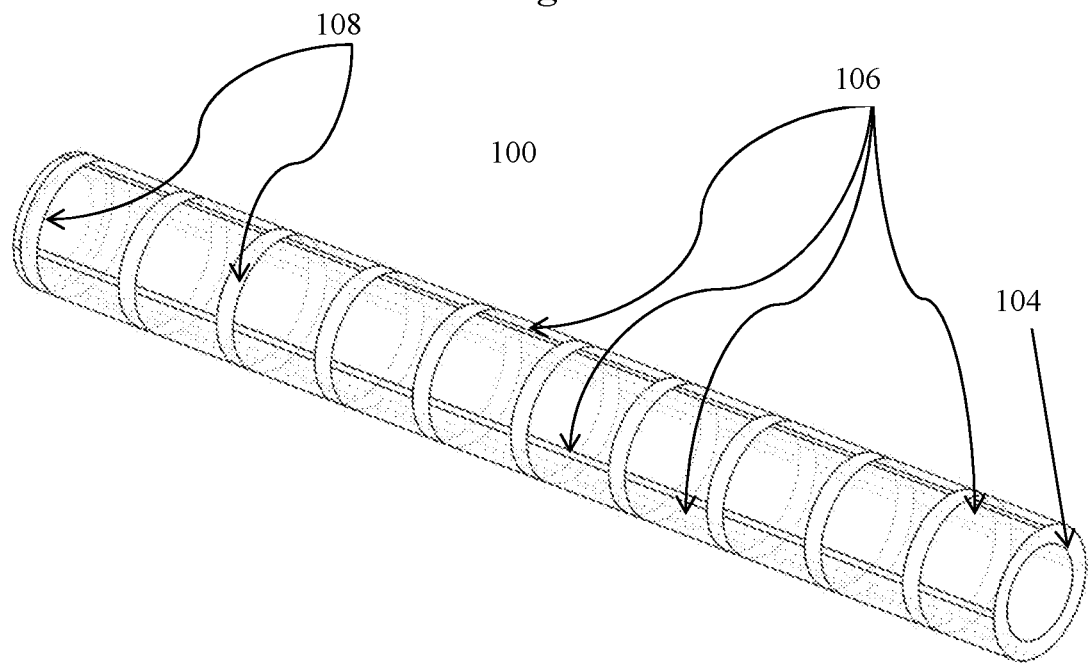
FIG. 2. Raw striped and ringed imaging window extrusion, isometric view.

Similarly, FIG. 2 shows a portion of the same probe 100 where an imaging window is shown in an isometric view. Two of the longitudinal marker elements 106 are visible around the circumference of the cylindrical tube 104. Additional longitudinal marker elements 106 may be provided as well. Thus, as the imagine core rotates within imaging window 110, the longitudinal markers are detected at regular angular, and therefore regular time intervals. For evenly spaced markers, this imaging core rotation will provide a longitudinal marker at any given location in a periodic fashion.

In this embodiment, circumferential marker rings 108 are also shown as a plurality of rings or bands surrounding the imaging window part of cylindrical tube 104. Circumferential marker rings 108 serve as reference points for longitudinal or 'stretch' distortion referred to in the art as (NULD). NULD is a less widely known type of image distortion that can occur if linear motion of imaging plane is non-uniform. However, the correction of NULD may also be of particular relevance in some embodiments. Thus, this embodiment contemplates a probe having both longitudinal marker elements 106 and circumferential marker rings 108 such that the both NURD and NULD can be corrected in images from the probe.

If NULD occurs, the longitudinal accuracy of the images is reduced, creating distortion of the image which could mislead the clinician and cause undesirable and sub-optimal results. By adding rings of fluorescent and/or scattering material with regular longitudinal spacing to the window, the system will detect these rings at regular time intervals during the imaging pull-back without NULD. If NULD exists the detection of the rings will not be regular, but varied, and the system will know that NULD exists. Software can then correct the spacing of the rings and also the morphological information from the anatomy as well to regular time intervals and therefore regular longitudinal spacing, moving the anatomical information as well, and in this way the system can correct for NULD.

Figure 3:
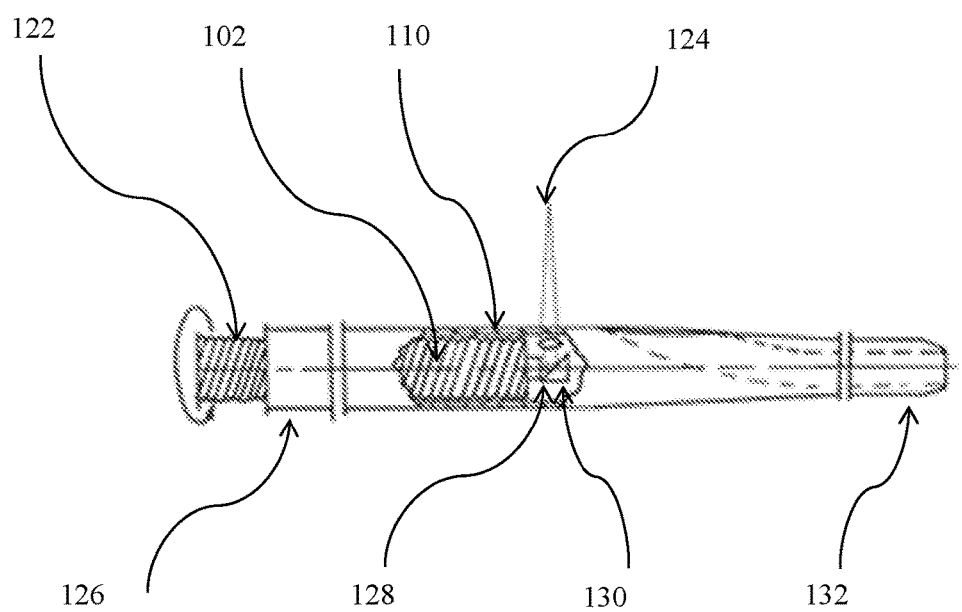
FIG. 3. Cross-sectional view of a catheter assembly distal end including imaging component, imaging plane and the distal segment of the catheter.

The image shown in FIG. 3 shows a partial cutaway view of the distal end of an exemplary catheter. Imaging core 102 is comprised of fiber optic connector (not shown), drive cable 122, fiber optic 128, and exemplary distal optics 130. The distal end will also include the marker elements (not shown in this embodiment). Imaging core 102 is located within catheter sheath 126, and particularly the imaging window portion, and is rotated and pulled back by the Patient Interface Unit (not shown) to create a three-dimensional image of the vessel of interest. The proximal end of the device (not shown) includes a catheter connector that mates with the Patient Interface Unit (PIU), which is connected to the imaging console via an electrical umbilical cord. Distal optics 130 are attached to optical fiber 128 and protected by the distal housing (not shown).

The same concepts that apply to conventional side-looking catheter probes as exemplified above are also applied to forward-looking catheter probes. Various types and locations of markers on the window element are detectable with existing optics and/or transducers that do not degrade the image from the user's point of view, including reticle lines, marks, dots, etc. These markers are positioned at equal or patterned angular intervals about the rotational axis of the device to provide angular position of the imaging elements at the imaging area at the distal end of the device. The system samples the angular deviation between these markers as the first step in detecting whether NURD exists. If the intervals between markers is uneven, NURD exists, and then the system software can move these markers, and the anatomical information associated with them back to the theoretical position as determined by the average rotational speed of the imaging core.

Markers elements do not substantially interfere with imaging detector performance. Thus, a signal created by the imaging core can be imaged by the imaging detector without substantial degradation in quality due to any interference from marker element signal. In some embodiments, the probe system includes two or more detectors, where the marker elements do not substantially interfere or degrade at least one detector that is an imaging detector. In one example, the system for OCT and fluorescence imaging includes an OCT detector and a fluorescence detector where the fluorescence detector is used to detect the marker elements and detects the marker elements at a wavelength that does not substantially overlap with the range or ranges used to detect the fluorescence image.

Some markers are not detectable within the wavelengths ranges used to image, but still detectable by the imaging system. In this case, the markers are not visible in the image the user sees, but markers could simply be physical marks on the surface of the window, and may be positioned outside of the field of view, or disposed within the window material itself, where the markers are visible to the user. For probes with the ability to image forward and side viewing, the markers can extend longitudinally along the imaging window portion of the device, and extend onto the distal window. Longitudinal markers could consist of detection fibers or other evenly spaced elements within the wall of the sheath.

Marker Elements

In some embodiments, the longitudinal marker elements 106 as well as the marker rings 108 are made from material, or contain materials that are substantially transparent to the imaging light (for example between 400 and 1500 nm or a region within this range). Thus, the signal from the longitudinal marker elements does not substantially interfere with imaging detector performance and does not detract from the imaging done by the detector element as it detects the image from the imaging component.

In some embodiments, an additional detector is used to detect the marker elements. Alternatively, the marker elements may be detectable with the imaging element, but occur outside the wavelength region critical to imaging. For example, the image may be obtained from light between 400 and 800 nm and the region between 800 and 1000 nm is used for detecting the longitudinal marker elements. In another example, the image may be obtained from light between 500 and 800 nm and the region between 400 and 500 nm is used for detecting the marker elements. Thus, when the system provides an image, for example, of a coronary artery, the marker elements will not be visible in the image. As used herein, the term "not visible to a detector element" means simply that, when observing an image obtained from the imaging component for the purpose of, for example, diagnosis of disease state (for either normal or optimal imaging), that marker elements will not interfere with the view of the image.

The marker elements 106 are depicted in FIG. 1 as semi-circular, forming half-cylindrical strips or rods along the cylindrical tube 106 axis, which is also the rotational axis of the probe 100. Similarly, marker elements 106 can be any desirable shape such as having circular, square, rectangular, or other cross section; can be on the outer surface of the cylindrical tube; or can be partially or fully in the cylindrical tube. They can, for example, be composed of scattering elements, or they can be the same material as the entire window extrusion material used to form a cylindrical tube but modified to be distinguishable from the remainder of the sheath material. This can be done, for example, by using ion bombardment.

In some embodiments, the width of the marker elements 106 is minimized, such as 20 μm to 200 μm, or 50 μm to 100 μm. Wider markers are possible, such as for larger diameter catheters, but the narrower marker elements 106 are preferred to reduce potential interference and to increase specificity.

Figure 4:
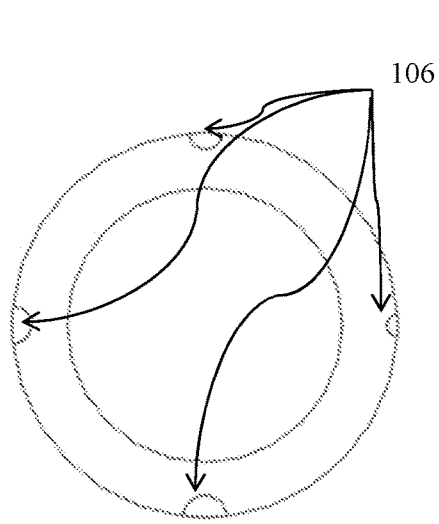
FIG. 4. Striped imaging window with varying width stripes, end view.

The longitudinal marker elements 106 must be adequately sized to be detected during rotation, and thus used to detect and correct NURD. However, the longitudinal marker elements (and similarly the circumferential marker rings) may be of varying width and/or area, so as to produce a signal that is different for each sector of the catheter. See, for example, FIG. 4, which provides four marker elements 106 having different dimension. The marker element width and cross-sectional area determine signal strength, so by varying the size of the stripes (e.g., varying one or more of width or height) the catheter can produce recognizable signal strength so the system knows at what sector the distal optics are pointing based on the intensity of the resulting marker signal. This additional information is particularly useful when there are cases of extreme NURD, where backlash can occur (the distal end of the imaging component and optics can actually move in the opposite direction from that of the proximal end) due to the extreme intermittent storage and release of rotational energy.

In this embodiment, four separate longitudinal marker elements 106 are shown. However, there may be 2, 3, 4, 5, 6, 7, 8, 9, 10, 11, 12, 13, 14, 15, 16 or more longitudinal marker elements 106 equally spaced around the outer surface 102 of the imaging window of the catheter sheath. Longitudinal marker elements 106 can be attached to outer surface 104. This may be accomplished by a number of different ways. For example, they may be adhered to the inner or outer surface of cylindrical tube 104. They may be co-extruded with the cylindrical tube, either as a different material or the same material with an additional dopant. They may be formed integral to the cylindrical tube 104 by, for example, lamination or co-extrusion. They may also be the same imaging window material.

In FIG. 2, longitudinal marker elements 106 extend the full length of the imaging window part of the cylindrical tube 104. In some embodiments, the longitudinal marker elements may extend more than the full length of imaging window 110 (such as for ease of fabrication). In other embodiments, longitudinal marker elements 106 may extend less than the full length of the imaging window 110, such as an extension of 80% of the window length. In yet other embodiments, the longitudinal marker elements 106 extend over only a portion of the imaging window.

In yet another embodiment, longitudinal marker elements 106 are located only at, for example, the very distal end of the imaging window. For example, they are located within 5 cm, within 3 cm, within 2 cm, or within 1 cm of the distal end of the imaging window. The system having this embodiment may only detect the marker elements at the very beginning of the imaging pull-back, and then when adequate NURD performance is confirmed, continues to image the anatomy by pulling the imaging core back out of the striped area of the window. This would be especially useful if the marker elements degrade the image in any way. Thus, in some embodiments as described herein, the plurality of marker elements do not interfere with the imaging detector performance because the marker elements are positioned such that they are not in the detection region during, for example, OCT pull-back. In these embodiments, the presence, absence, or amount of NURD is detected prior to pullback but not during the imaging process.

In yet another embodiment, the longitudinal marker elements are not located at the very distal tip of the cylindrical tube but instead are offset from the tip of the tube. In some embodiments, the longitudinal markers extend for substantively the entire length of the imaging window. This is particularly useful for, for example, detecting NURD during the entire pull-back for OCT imaging.

In some embodiments, the marker elements 106 may be provided in a patterned arrangement. For example, in addition to a number of equally spaced markers, an additional marker is provided at one location. In some embodiments, the marker elements integral with the imaging window and made from a doped material have varying levels of dopant. In another example, one marker element may contain more dopant than the other marker elements such that, when the fluorescence is detected, the level for the one marker element is measurably greater. These variations allow the system to know at what sector the distal optics are pointing based on the added or different signal of the resulting marker signal.

In some embodiments, the marker elements may be combined into a single (or several) units with varying marker intensities. For example, a ring-shaped unit may contain a plurality of distinct longitudinal regions areas having a higher level of dopant that can be detected as the ring rotates around the rotational axis. Another example includes a ring-shaped unit with a sinusoidal concentration of scattering particles to provide a varying amount of scatter as the ring is rotated about the rotational axis.

In some embodiments, a variance in the circumferential marker rings 108 (either via varying the width and/or area, providing a patterned spacing, or varying doping) can be used to provide information on linear position. This can be used, for example, during pullback of an OCT probe.

The marker elements are detectable by the system. In some embodiments, the marker elements are visible via fluorescence. In other embodiments, the marker elements are visible via light scattering. The marker elements may be made out of, for example, the same extrusion material as the imaging window with the addition of a colorant or dopant. Such colorants and dopants are well known to those skilled in the art, and can be tailored, for example, to produce a signal that is outside the wavelength ranges of interest in the detection of vulnerable plaque, and other morphological tissue or vascular disease states of interest.

In some embodiments, the marker elements are visible via differences in absorption. For example, a marker may contain a component with a high extinction coefficient and thus can be detected by changes in absorption.

The marker elements are distinguishable from the remainder of the imaging window. Thus, the time intervals between the detections of the plurality of marker elements during rotation can be counted. The difference in the time intervals of equally spaced markers can then be corrected and thus, the NURD or NULD (with the addition of marker rings) can be corrected.

The imaging detection system is configured to detect the difference between the majority of the window material and the marker elements and/or marker rings. For example, fluorescence detection at a wavelength different from the fluorescence maxima or wavelengths for the image viewing region. The fluorescence detection may be set at a wavelength or wavelength range outside the range of both natural tissue auto-fluorescence wavelength ranges, and also outside the dye-induced fluorescence wavelength ranges if Near Infrared Fluorescence (NIRF) detection is included in the system. This allows detection of the marker elements that does not interfere with optimal imaging of anatomy that is critical to the diagnosis, such as the diagnosis of cardiovascular disease.

As the distal optics scan past a longitudinal marker element, the marker element causes an higher level or 'bump' in the level of fluorescence, scattering, etc. The system software is provided to count the time intervals between these 'bumps' in signal levels, such as bumps in fluorescence or scattering levels (s). The marker elements are preferably evenly spaced angularly and are therefore regularly detected on a time basis as the imaging component rotates through a complete revolution to collect a single image frame. The marker rings are similarly evenly spaced along the axis and are also regularly detected as the imaging component pulls back during an imaging pull-back.

If the timing between these 'bumps' in intensity is not even and regular, then NURD and/or NULD has occurred which will distort the image, and software will need to correct the spacing to correct for NURD and/or NULD.

Probe and System

The probe as described herein may be a catheter where the cylindrical tube is the catheter sheath. An imaging component is inside the catheter, where the imaging component can image in vivo via OCT, fluorescence, IVUS, or other imaging methods. The imaging catheter may be adapted for creating a cross-sectional image from an in vivo sample. In some embodiments, the imaging component consists of a connector, drive shaft, optical fiber and distal optics, which are rotated and pulled back inside of the catheter sheath (the cylindrical tube), which stays stationary during imaging. When deployed in a blood vessel, the system can produce a 3-D reconstruction of the blood vessel for, for example, diagnosis of coronary artery disease, or other areas of the body of interest to the clinician such as gastrointestinal (GI), urological (URO), biliary tree, peripheral vasculature, neurological, etc.

The cylindrical tube includes an imaging window 110 at the distal end through which light from the imaging component is transmitted into the surrounding tissue forming an imaging plane 124 as the imaging core 102 is rotated (FIG. 3). The imaging window may be, for example, a cylindrical polymer extrusion suitable for use in the coronary vasculature, wherein an imaging component rotates and pulls back to create a 3-D image. The imaging window is substantially transparent to imaging light (for example light between 400 and 1000 nm or a region there within).

Figure 5:
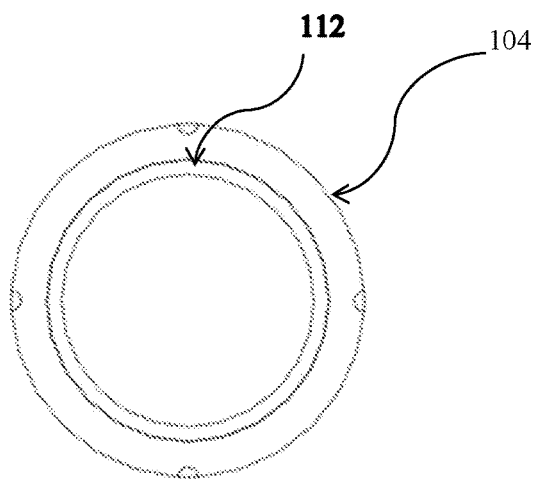
FIG. 5. Tri-extrusion With Inner, Lubricious Layer, end view.

Another embodiment employs an additional liner in the cylindrical tube. For example, a tri-extrusion can be used to form a second or third material into an inner liner 112 of the cylindrical tube 104 that is more lubricious with lower frictional properties and better wear properties. This layer, as shown in FIG. 5, facilitates ideal imaging with a high-speed, rotating imaging core. Preferably, all materials used in forming lubricious layer 112, and imaging window 104 are optically transparent and of low fluorescence in the electromagnetic wavelength range between 400 nm and 1500 nm.

In some embodiments, the imaging window has a hydrophilic coating on its outer surface. This provides for facile movement of the catheter probe through an in vivo environment. A lubricious material may be provided on the inner surface of the imaging window (e.g., FEP, or PTFE (Teflon®) to allow the imaging core to rotate freely within the imaging window.

Imaging and Processing

Since the system knows where the fluorescence from the marker bands should be located if there is no distortion, the system can correct for NURD, repositioning portions of the image in their proper quadrant using software.

Although not intended to limit the scope of the embodiments of the present invention, the following general discussion may be helpful for understanding various mathematical and physical principles underlying some embodiments. Assume that between each two adjacent marker elements, the angular motion can be approximated by an uniformly accelerated angular motion. According to some to various embodiments, four equations can be used to describe the non-uniform angular motion within a full rotation as:

$$\Delta\theta_1 = \omega_0 T_1 + \alpha_1 \frac{T_1^2}{2}$$

$$\Delta\theta_2 = (\omega_0 + \alpha_1 T_1)T_2 + \alpha_2 \frac{T_2^2}{2}$$

$$\Delta\theta_3 = (\omega_0 + \alpha_1 T_1 + \alpha_2 T_2)T_3 + \alpha_3 \frac{T_3^2}{2}$$

$$\Delta\theta_4 = (\omega_0 + \alpha_1 T_1 + \alpha_2 T_2 + \alpha_3 T_3)T_4 + \alpha_4 \frac{T_4^2}{2}$$

where $\Delta\theta_i$ is the angle between two adjacent marker bands and is $$\frac{\pi}{2}$$

for equal width marker bands.

$\omega_0$ is the angular velocity at the beginning of the first strip.

$\alpha_i$ is the average angular acceleration between two adjacent marker bands.

$T_i$ is the time measurement between the two adjacent bumps.

Assuming the angular velocity goes back to the beginning value such that at the distal end the NURD variation will repeat itself from frame to frame after a short transition period, a fifth equation can be obtained as:

$$\alpha_1 T_1 + \alpha_2 T_2 + \alpha_3 T_3 + \alpha_4 T_4 = 0$$

Five equations can be used to solve for the five NURD related variables: $\alpha_1$, $\alpha_2$, $\alpha_3$, $\alpha_4$, and $\omega_0$. Once the NURD variables are computed, the image scan lines can be resampled to compensate for the NURD effect.

Another reference that can be utilized for the detection and correction of NURD is the 'A-line'. This is the angular position associated with each sampling position (500 per revolution) of the imaging core and therefore the distal optics as they rotate through one frame, or 360 degrees of rotation. The system estimates the angular position of longitudinal marker elements, forming an estimation matrix. The system then updates the estimation matrix and compares the detected angular position of the longitudinal marker elements with the theoretical angular position of the longitudinal marker elements. The system then moves the A-lines associated with those longitudinal marker elements that are out of position (their position varies from the theoretical position based on average rotational speed) to coincide with the theoretical position, thusly correcting the angular distortion (NURD).

NURD and NULD

In some embodiments, the imaging window is constructed where the marker elements are longitudinal stripes located at regular angular intervals around the cylindrical tube such that as the imaging core containing the imaging component rotates through each complete rotation, the stripes are detected at regular time intervals if the rotation speed is constant and the system has no NURD. If NURD exists, the time intervals between the intermittent detection of the stripes will not be regular, but varied due to the variance in rotational speed. By computing the difference between the varied intervals detected and the expected intervals of the known rotational speed, NURD can be detected. By using software to reposition the marker elements and corresponding 'A'-lines at regular time intervals, therefore regular angular intervals, NURD can be corrected.

Figure 6A:
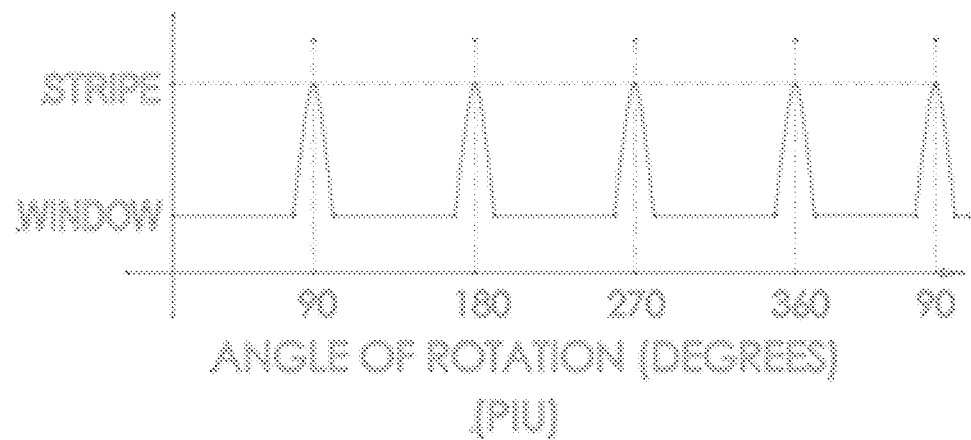
FIGS. 6(A)-6(B). Intermittent signal from striped catheter; no NURD (FIG. 6(A) and with NURD (FIG. 6(B)).
Figure 6B:
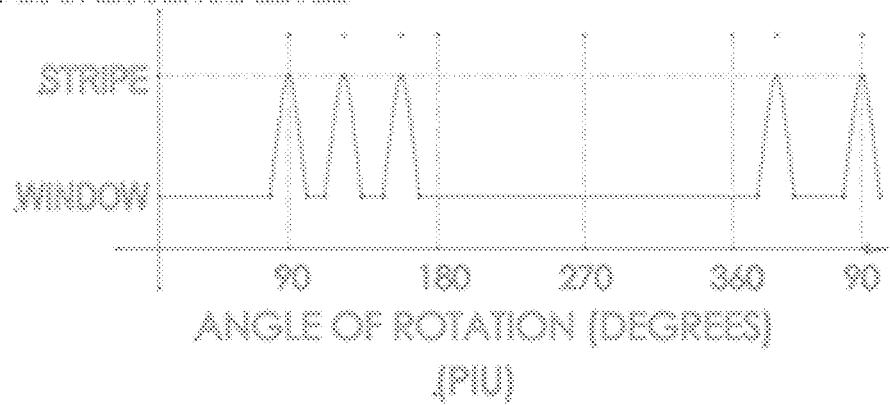
Figure 7A:
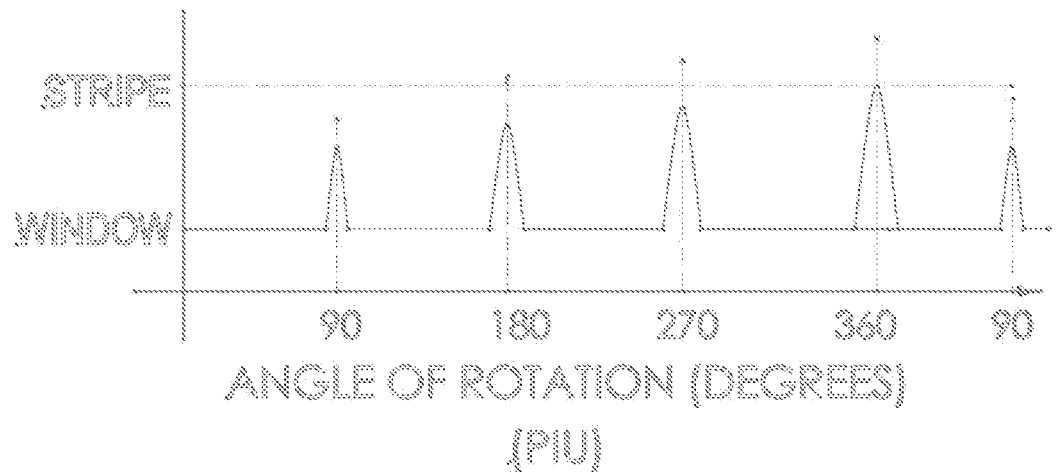
FIGS. 7(A)-7(B). Fluorescence or signal-scattering levels graph with varying width stripes; no NURD (FIG. 7(A)) and with NURD (FIG. 7(B)).

FIGS. 6(A)-6(B) and 7(A)-7(B) show relative fluorescence levels of the colored or doped stripes compared with that of the remainder of the imaging window, shown as a function of the angular position of the motor at the proximal end of the device. FIG. 6(A) represents the fluorescence level using identically sized marker elements and FIG. 7(A) represents fluorescence levels of marker elements of varying size and therefore the signal strength received from each marker element also varies as shown. However, both figures show a regular pattern of increased intensity and indicate that no NURD is present.

Figure 7B:
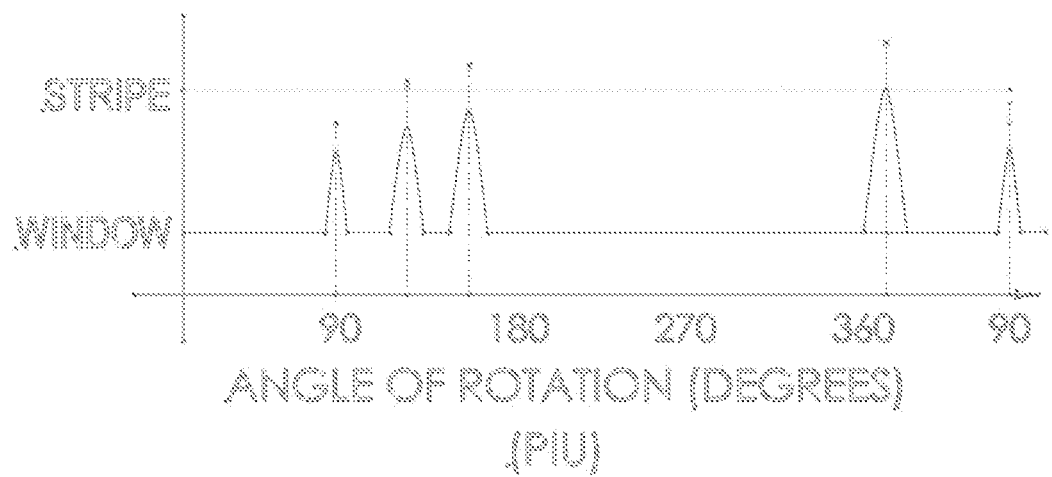

If there is no NURD present, as exemplified by FIG. 6(A) and FIG. 7(A), the 'bumps' in fluorescence level coincide with the known angular position, but if NURD is present as exemplified in FIG. 6(B) and FIG. 7(B), they do not. Since the imaging computer only knows the angular position of the proximal end of the device via encoder, etc., it assumes the angular position of the distal end, i.e., distal optics. By providing a means to detect relative angular position of the distal end, the presently described embodiments provide for the detection and correction of NURD. In other words, if the relative angular position of the fluorescent stripes changes or shifts during a single rotation or frame, or if their relative position shifts over short intervals of time, the system knows that NURD exists, and can correct the NURD by placing the angular position of those stripes, and also the information from the anatomy included in the images back to the known angular position of the motor and proximal end of the device, thusly correcting the NURD.

FIG. 7(A) shows relative fluorescence levels of the marker elements during rotation without NURD where the different marker elements have varying widths. The varying fluorescence levels of the marker elements compared with that of the remainder of the imaging window, shown as a function of the angular position of the PIU or motor at the proximal end of the device can be seen. The 'bumps' in fluorescence level, signal or light-scattering levels are detected at regular intervals, and coincide with the known angular position. This provides differing intensities of the fluorescent signal and allows for actual orientation information (e.g., the highest intensity or widest stripe corresponds to a certain orientation of the cylindrical tube.) However, regardless of the width of the marker elements, the even spacing compared to the PIU angle of rotation can be seen. In contrast, FIG. 7(B) illustrates when NURD is present and the fluorescent intensities do not correspond with the angle of rotation. Since the system knows where the fluorescence from the stripes should be, it can correct for NURD, repositioning portions of the image in their proper quadrant.

In yet another embodiment, the NURD detection system is for use with OCT or IVUS imaging alone, with no fluorescence detection or fluorescent stripes in the catheter imaging window. This is accomplished via the addition of light-scattering particles, microspheres, material of different or varying refractive index, surface modification, etc., that are detectable with either OCT or IVUS imaging without degrading the image. These marker elements form stripes located at regular angular intervals about the periphery of the imaging window. The same variations listed above regarding stripe width and/or density of particles apply to these embodiments to effect the correction of NURD.

In some embodiments, the fluorescence signals used to detect NURD are detected by the same detectors used to detect image information. In these embodiments, the NURD detection detector may be identical to the imaging detector but equipped with the appropriate filter or filters to allow only those wavelengths desired from the marker elements. Alternatively, the NURD detection detector is the imaging detector, again with appropriate filters to allow only the signal from the marker elements to pass while the remainder of the signal is used for imaging.

In some embodiments, a separate detector or detectors are used to detect the fluorescence signals for NURD are separate from the detectors used to obtain the image information.

Methods of Making

One method of creating detectable stripes in the imaging window material is via co-extrusion. Co-extrusions are well known in the art, and are generally comprised of two different but similar materials that are extruded at the same time, through the same extrusion machine. Generally co-extrusions are thought of as concentric layers on a single lumen tube, but variations are possible via tooling that allow a wide variety of configurations utilizing two or more different polymers. In this case the cylindrical co-extrusion consists of two optically transparent materials with similar refractive index, with one material forming the stripes and/or rings used for NURD and/or NULD detection and the second material forming the remainder of the cylindrical window extrusion. The co-extrudate for the marker elements may be the same material as used to form the window but with a higher or lower amount of a dopant.

Another way to construct the imaging window involves the use of one material to form both the stripe areas and the remainder of the extrusion body. The marker elements are formed after the extrusion is produced, and added by being colored, doped, painted on, roughened or otherwise modified surface, ion implanted or injected with fluorescent and/or scattering material so as to produce equally spaced lines or stripes. Both the inner diameter and outer diameter of the co-extrusion are smooth, cylindrical diameters and both striped areas and the remainder of the window are made with materials that have similar index of refraction so as not to interfere with optical imaging.

The stripes can be added to the raw extrusion, which is then post-processed through various forming methods known to those skilled in the art into a functional catheter imaging window and rapid exchange segment. The imaging window may be subsequently attached to the mid-segment of the catheter as shown in FIG. 5 to form the working length of the catheter. Also possible is the addition of stripes after the catheter is post processed, but preferably before, for example, a hydrophilic coating is added to the outer diameter.

In yet another embodiment, the marker elements are added to the imaging window after an extrusion process forms the imaging window (or where the imaging window is formed by another means) via various processes including but not limited to; painting, ion implantation, material modification, doping, addition of fluorescent and/or scattering particles such as microspheres, bismuth, barium sulphate, metallic particles etc., which are well known to those skilled in the art. In this way the extrusion itself can be simple and single layer, not requiring co-extrusion. The same variations to stripe width and density (above) for NURD correction purposes applies to these methods of creating fluorescent and signal-scattering stripes as well. The markers should be rendered to be detectable by existing optics and transducers to allow the system to detect the angular position of the distal optics and/or transducers.

Applications

Figure 8:
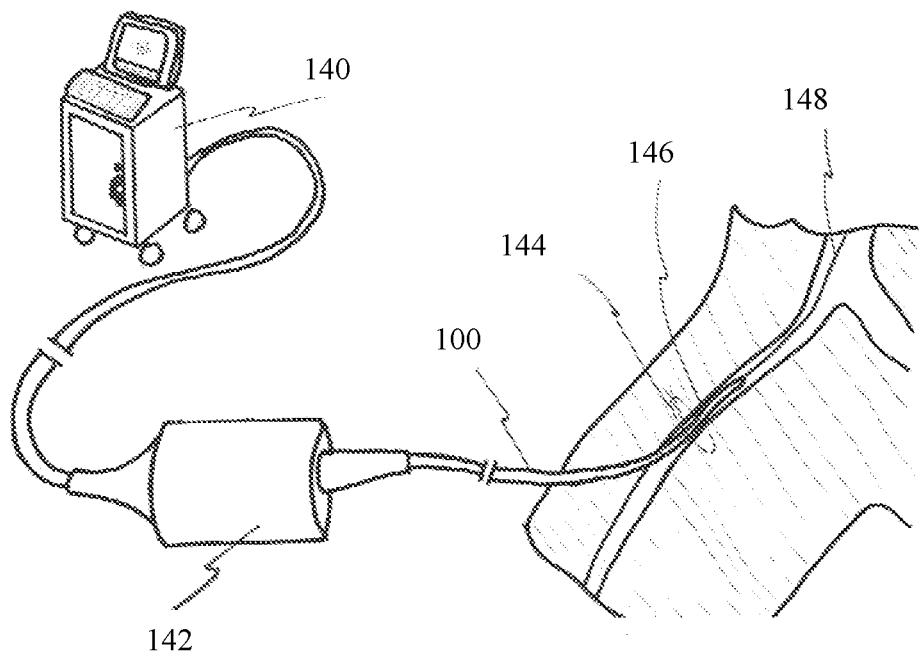
FIG. 8. An embodiment showing a system used in a blood vessel including an imaging console, motor drive, and catheter probe.

One application for the probe as described herein is for an OCT probe used in coronary vasculature for diagnosis and/or treatment of coronary diseases and conditions. The system used for this application is shown in FIG. 8. The system includes an imaging console 140 which includes, for example, a computer, a light source and a detector that can be used to detect and correct the NURD based on the angular velocity information obtained from the marker bands. The imaging console 140 is connected to a motor drive 142 which rotates the imaging core forming imaging plane 144. The motor is rotated at rotational speed R. This speed should be substantially consistent through the image acquisition. The probe is inserted into a blood vessel 146 and guided to the site of interest by means of a guidewire 148. Then, the imaging core can undergo pullback where the imaging plane 144 moves along the imaging window 110 where images of the surrounding tissue are obtained.

Figure 9:
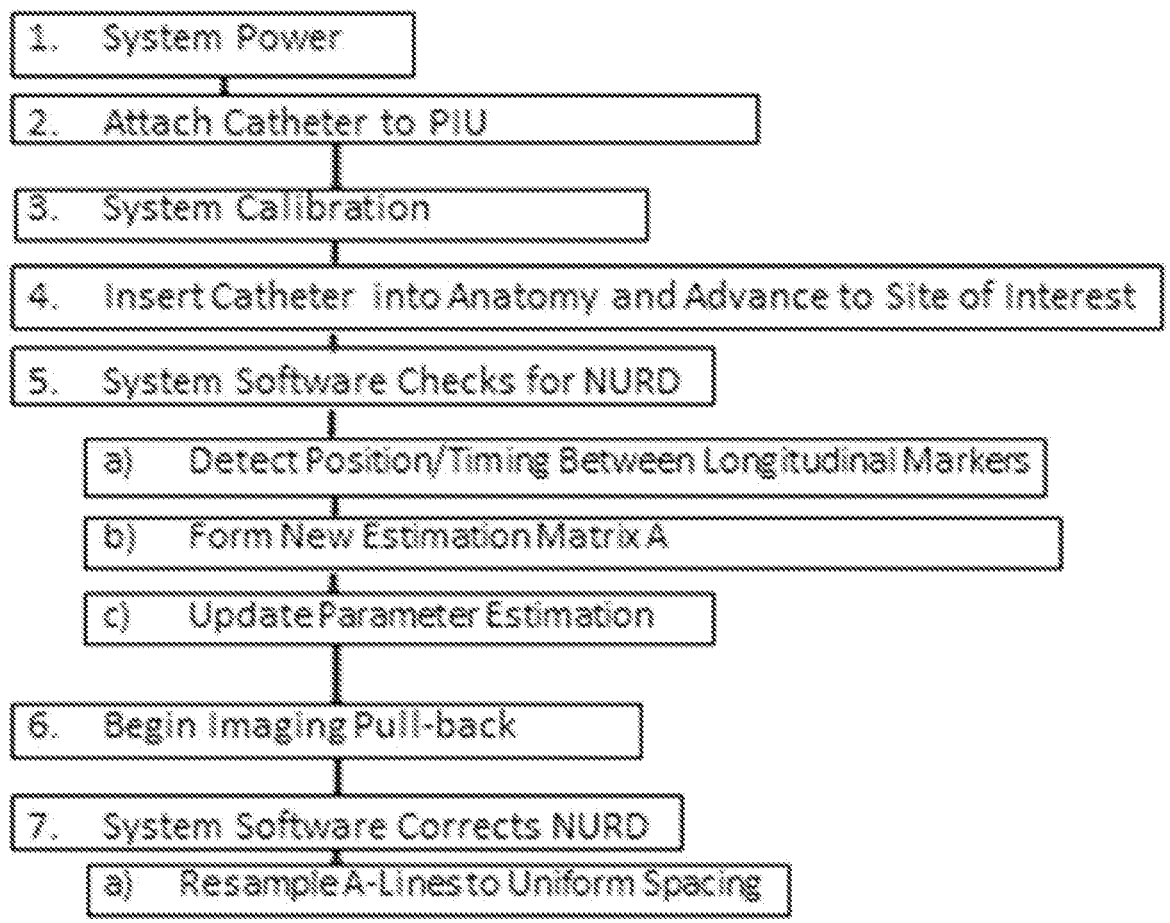
FIG. 9. Exemplary NURD detection and correction flowchart.

A flow chart of an exemplary embodiment is shown in FIG. 9. After the pre-insertion steps, starting at step 4, the catheter is inserted into the anatomy and the system is ready to perform the imaging pull-back. Before pull-back, the system first checks for NURD. The system and software detect the apparent angular spacing of the markers. To summarize these marker positions and therefore the angular spacing and thus the time elapsed between markers, the system software forms New Estimation Matrix A. The software then updates the Parameter estimation. At that point, the system begins the imaging pull-back, checking the angular spacing between markers, and entering the data into the estimation matrix. If NURD exists, the system moves 'out of place' markers and anatomical image information along with the markers, moving them back to their theoretical position based on computed location assuming constant rotational speed.

Figure 10:
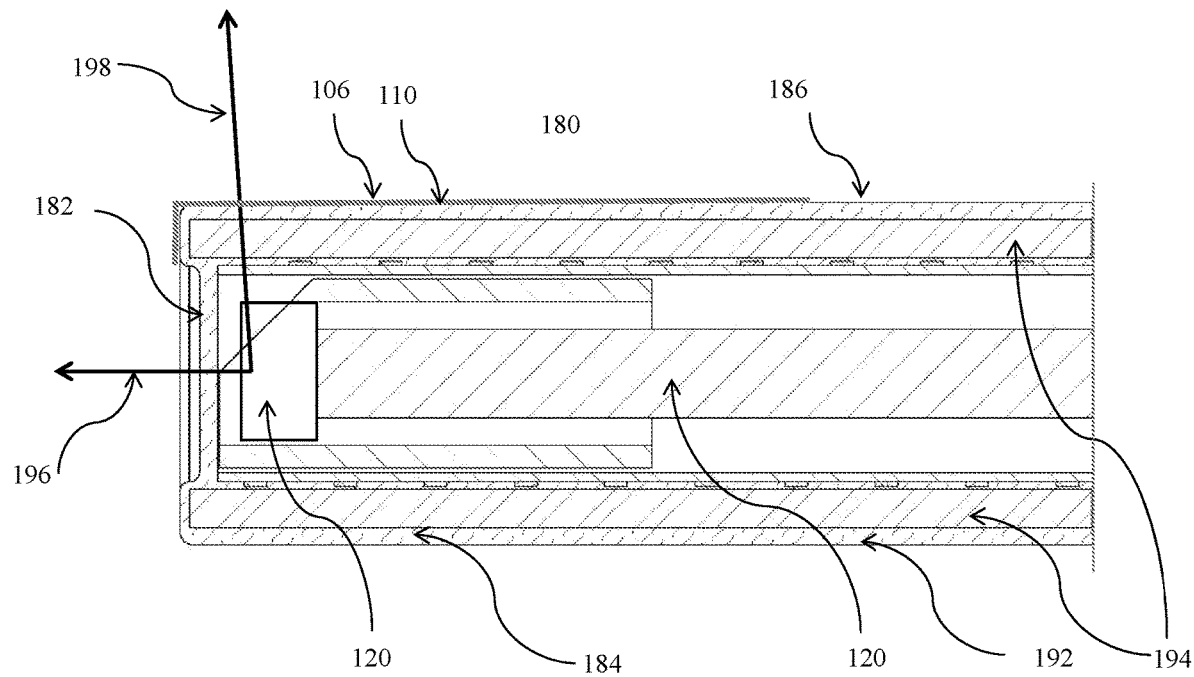
FIG. 10. An exemplary OCT catheter probe in a cross-sectional view.

Referring to FIG. 10, an exemplary OCT catheter probe 180 equipped with an optional forward view direction 196 and side viewing direction 198 imaging capabilities shown in cross-sectional side view. This embodiment shows an imaging component 120 (the optical fiber portion of the imaging core is shown here without any torque component) and cylindrical tube 104, sheath and window material 184 covering the face of optical fibers 194. Side view window 110 includes longitudinal markers 106 (only a single marker shown in cross section) similar to those in previous embodiments, but extend onto forward viewing window 182 to provide angular reference as in previous embodiments. Both longitudinal markers, which may optionally extend partially or fully over the distal end of the probe to form radial ends detectable from a forward viewing window, and optionally separate radial markers on forward viewing window are detectable with imaging detector or secondary detector arranged with appropriate filters. Alternatively, markers can be physically positioned out of the field of view, or are constructed of a material that is detectable with wavelength ranges that are beyond the ranges needed for imaging.

Figure 11:
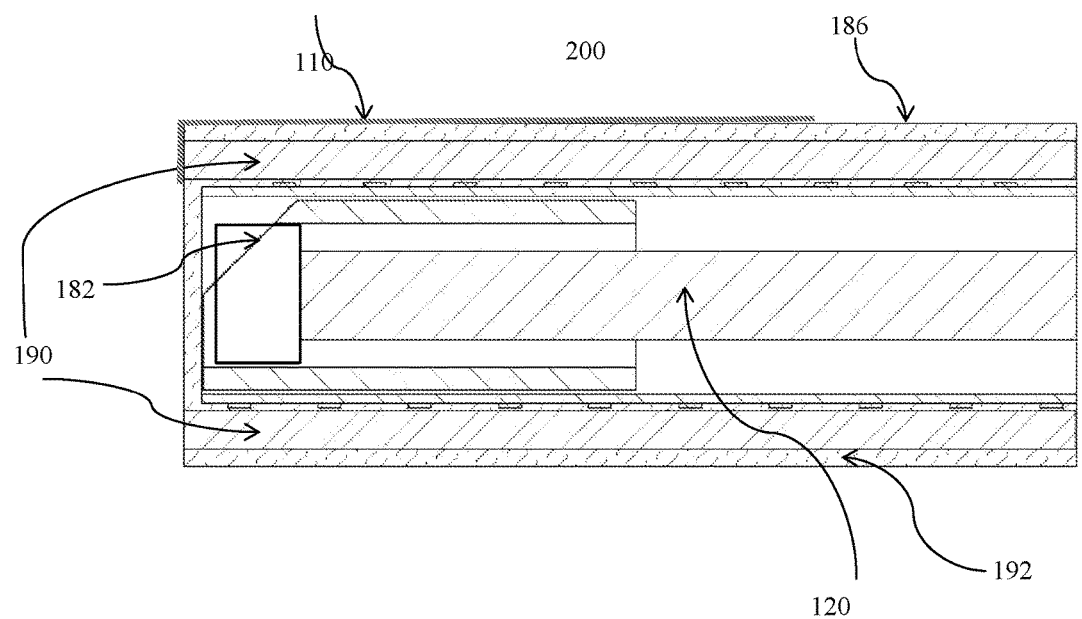
FIG. 11. An exemplary SEE forward view catheter probe in cross-sectional view.

Referring to FIG. 11, an exemplary spectrally encoded (SE) catheter probe 200 is shown in cross-section isometric view. In this embodiment optical fiber faces 190 are not covered with sheath or window material 192, but are exposed. In addition to the window 110, a forward-viewing imaging window 182 is positioned perpendicular to the axis of the device to allow imaging axially out the window in a substantially axial direction. In this embodiment, exemplary forward-view SEE imaging components 120 are provided. However, other probes are similarly contemplated for use in the probe as discussed herein. For example, systems as disclosed in, for example, WO2015/116951, WO2015/116939, WO2017/024145, U.S. 2017/0035281, and pending application Ser. No. 15/430,205 may be used in conjunction with the present invention.

The distal end only of forward and side viewing catheter probe 180 is shown in FIG. 11 in isometric cross-section. Both catheter sheath 192 and imaging component 120 are shown foreshortened for simplicity, where both sheath 192 and imaging component 120 extend substantially in the proximal direction to form catheter probe 180. In some embodiments, the overall length of the catheter probe is on the order of 1.50 meters. Forward viewing window 182 is integral with side viewing window 184, which extends proximally along catheter outer diameter 186 from, for example, 0.25 mm up to the full length of the device. For probes that include both forward and side viewing capabilities, imaging component 120 would need to be equipped with both forward and side viewing optics 190, and if desired, catheter probe 180 has the ability to perform and imaging pull-back, which moves the core proximally within the stationary sheath 192. Imaging windows 182 and 184 may optionally cover detection fibers (194, not shown in this figure) within the wall of catheter sheath 192, or the coating may be polished away, exposing and optionally polishing the distal face of detection fibers (not shown). Imaging windows 110 and 136 may be integral, applied onto catheter sheath 192, may be separate, such as with a polymer, glass or sapphire window material separate and different from the material that forms catheter sheath 102, or optionally the same material as catheter sheath 192.

Figure 12:
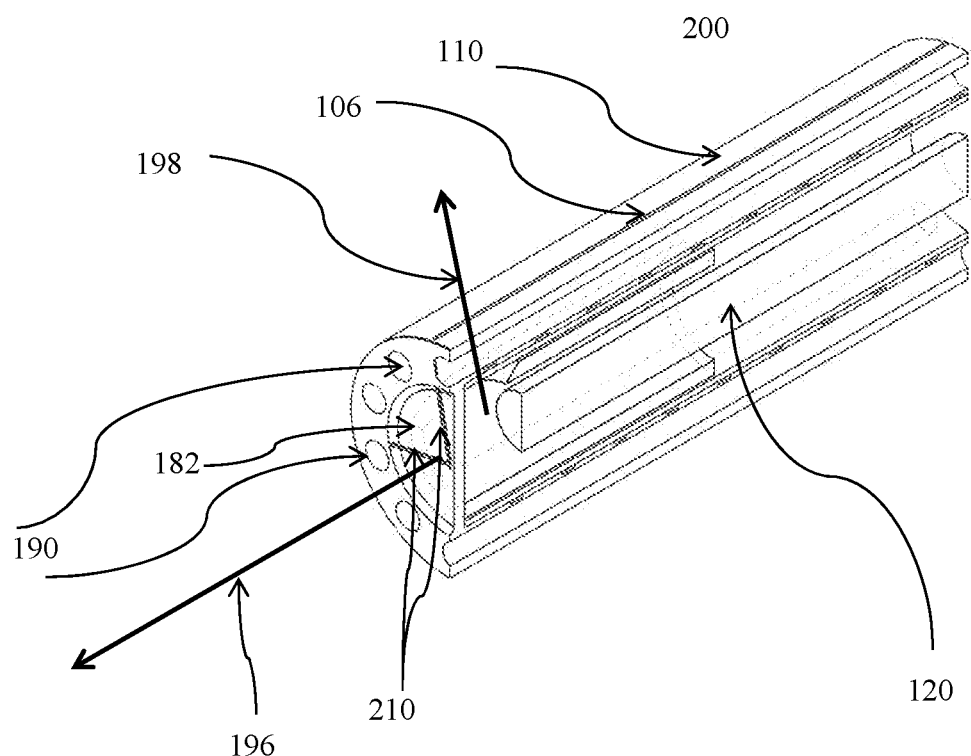
FIG. 12. An exemplary forward and side view in isometric cross-section view.

In FIG. 12, front and side viewing catheter probe 200 (e.g., a SEE probe) is shown in isometric cross-section. Longitudinal markers 106 are equally spaced around side view window 184, and may be extended onto front viewing window 182. When imaging in side view direction 198 imaging component 120 scans radially, detecting longitudinal markers 106. System software samples the angular spacing between markers, and computes the amount of NURD exhibited by the probe. When imaging in front view direction 196, imaging component 120 scans substantially axially, detecting radial marker elements 210 as it rotates. System software again samples angular spacing between detected radial markers 210 and computes the amount of NURD exhibited by the probe. Similar to previous embodiments, markers can be fluorescent, light-scattering, colored, ion-bombarded, or positioned out of the field of view from the users perspective, and as such, not seen by the user in the image.

In some embodiments, as part of user feedback related to NURD detection, it is desirable to display a message or image on the system screen that notifies the user regarding the existence and extent of detected NURD, or the absence of NURD. This message may state something to the effect of 'No NURD Present', or 'NURD=<X %', etc. Thus, when NURD is absent, there may be no NURD correction during pullback.

Figure 13:
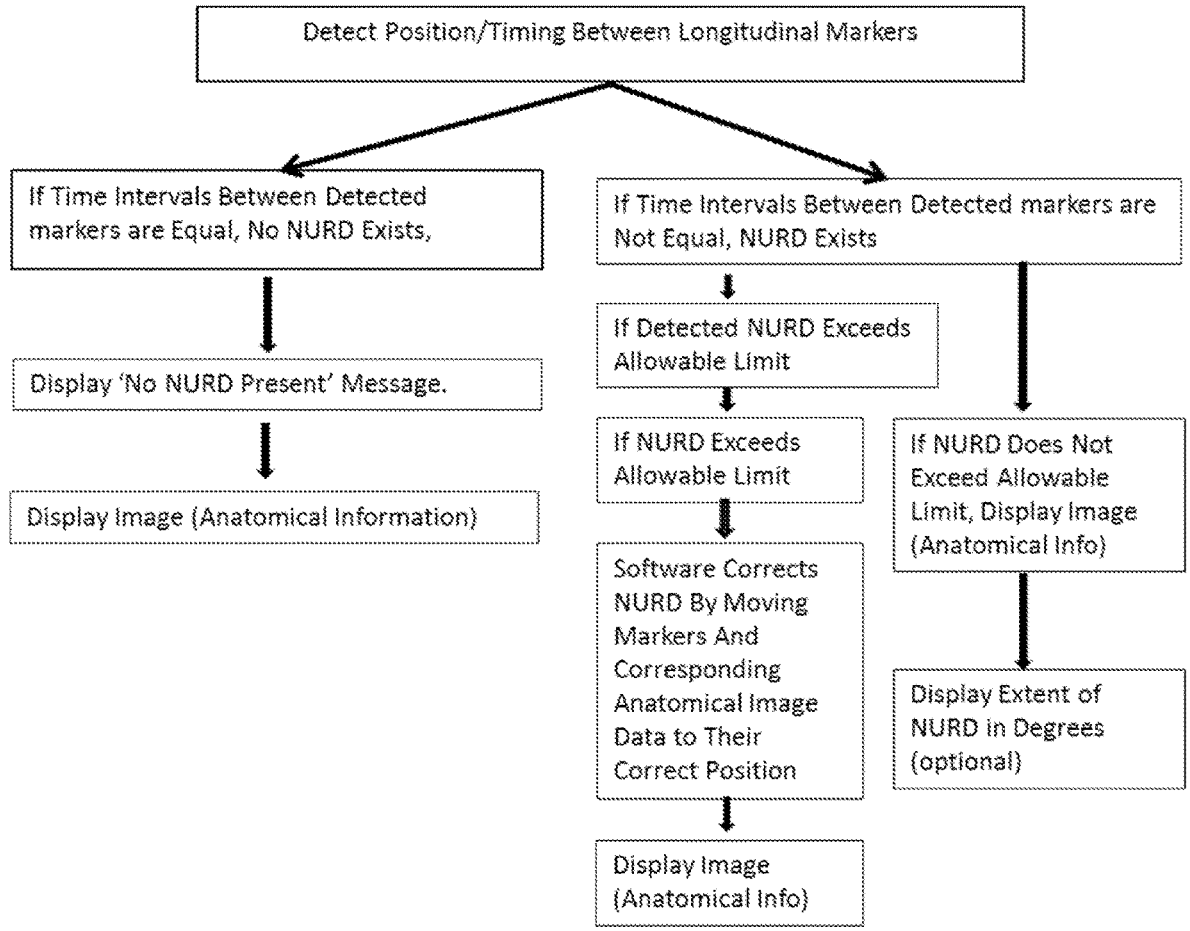
FIG. 13. Portion of the exemplary NURD detection and correction flowchart expanded and including lay terms.

FIG. 13 shows an alternate flow chart using layman's terms for the system software checking for NURD. This flowchart begins with detecting the position and/or timing between longitudinal markers to determine the existence and/or extent of NURD.

Embodiment(s) of the present invention can also be realized by one or more computers that reads out and executes computer executable instructions (e.g., one or more programs) recorded on a transitory or non-transitory storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer system, for example, is part of or attached to the imaging console and can obtain and modify information received from the imaging detector and an optional second detector.

In one embodiment, the imaging console 140 includes a computer unit and one or more display units are connected to the console 140 via a high definition multimedia interface (HDMI). Optionally, a separate image server is another computer unit connected to the console 140 connected via an Ethernet cable or the wireless access point.

Figure 14:
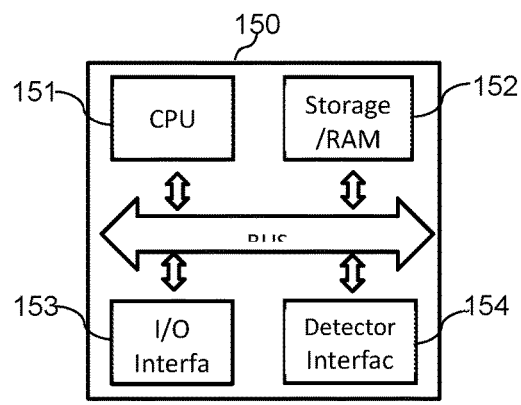
FIG. 14. A computer unit of an embodiment as described herein.

The computer units can be described by FIG. 14 where a command can be transmitted to the computer system 151 via a user interface unit/arrangement that may be located on the imaging console 140. A touch panel screen can be included as part of the user interface unit/imaging console, but key board, mouse, joy-stick, ball controller, and foot pedal can also be included. The user can cause a command to be initiated to observe inside the human body through the exemplary front-view SEE probe using the user interface unit/imaging console. For example, when the user inputs a command, the command is transmitted to the central processing unit for execution thereby.

Computer system 150 can include CPU 151, Storage/RAM 152, I/O Interface 153 and Detector Interface 154. Also, Computer system 150 may comprise one or more devices. For example, the one computer may include components 151, 152 and 153 and other computer may include component 154.

The CPU 151 is configured to read and perform computer-executable instructions stored in the Storage/RAM 152. The computer-executable instructions may include those for the performance of the methods and/or calculations described herein. For example, CPU 151 calculates the angular momentum and uses that information to correct the NURD and provide a new set of image where their angular positions are corrected. Storage/RAM 152 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 152 may store computer-readable data and/or computer-executable instructions. The components of the computer system 150 communicate via a bus.

The I/O interface 153 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The detector interface 153 also provides communication interfaces to input and output devices. The detector may include, for example a photomultiplier tube (PMT), a photodiode, an avalanche photodiode detector (APD), a charge-coupled device (CCD), multi-pixel photon counters (MPPC), or others. Also, the function of detector may be realized by computer executable instructions (e.g., one or more programs) recorded on a Storage/RAM 152.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A probe comprising:
    a rotatable imaging core comprising an imaging component and having a rotational axis;
    a cylindrical tube surrounding the imaging core, having the same rotational axis and having a proximal end, a distal end, and a lumen extending therebetween, the distal end of the cylindrical tube comprising:
        an imaging window, and
        a plurality of longitudinal marker elements integral with or attached to the imaging window and arranged parallel to the rotational axis,
    wherein the plurality of marker elements are not visible in an imaging detector.

2. The probe of claim 1, wherein the plurality of longitudinal marker elements form longitudinal stripes on the imaging window.

3. The probe of claim 1, wherein the plurality of longitudinal marker elements are located at equal angular intervals around the imaging window.

4. The probe of claim 1, wherein the plurality of longitudinal marker elements are located within five cm of the distal end of the cylindrical tube.

5. The probe of claim 2, wherein there are at least four longitudinal marker elements.

6. The probe of claim 1, further comprising a plurality of marker rings arranged circumferentially and that are equally spaced along the imaging window.

7. The probe of claim 1, wherein the plurality of longitudinal marker elements are each less than 15 degrees and more than 0.50 degrees in width.

8. The probe of claim 1, wherein the plurality of longitudinal marker elements are light-scattering marker elements or fluorescent marker elements.

9. The probe of claim 1, wherein the plurality of longitudinal marker elements vary in thickness or fluorescent intensity along a length of the marker element.

10. The probe of claim 1, wherein both the cylindrical tube and longitudinal marker elements were formed together via a polymer co-extrusion process.

11. The probe of claim 1, wherein an imaging element of the imaging component is an optical coherence tomography (OCT) imaging element and the longitudinal marker elements are longitudinal scattering elements.

12. An imaging catheter system comprising:
    a rotatable imaging core comprising an imaging component and having a rotational axis;
    a cylindrical tube surrounding the imaging core, having the same rotational axis and having a proximal end, a distal end, and a lumen extending therebetween, the distal end of the cylindrical tube comprising:
        an imaging window, and
        a plurality of longitudinal marker elements integral with or attached to the imaging window and arranged parallel to the rotational axis,
    an imaging console connected to the proximal end of the cylindrical tube, and
    at least one detector,
    wherein the plurality of marker elements are not visible in an imaging detector.

13. The imaging catheter system of claim 12, wherein the imaging console is configured to form 3-dimensional images.

14. The imaging catheter system of claim 12, wherein the detector is configured or adapted to detect an apparent rotation angle of the plurality of longitudinal marker elements with respect to each other.

15. The imaging catheter system of claim 12, further comprising a plurality of marker rings arranged circumferentially and that are equally spaced along the imaging window.

16. The imaging catheter system of claim 12, wherein the imaging core is adapted or configured for forming a cross-sectional image of an in vivo sample.

17. The imaging catheter system of claim 16, wherein an imaging element of the imaging component is an optical coherence tomography (OCT) imaging element and the longitudinal marker elements are longitudinal scattering elements.

18. A method of monitoring non-uniform rotational distortion (NURD) comprising:
    (a) rotating a rotatable imaging core of a probe, where the probe comprises:
        the rotatable imaging core comprising an imaging component and having a rotational axis;
        a cylindrical tube surrounding the imaging core, having the same rotational axis and having a proximal end, a distal end, and a lumen extending therebetween, the distal end of the cylindrical tube comprising:
            an imaging window, and
            a plurality of longitudinal marker elements integral with or attached to the imaging window and arranged parallel to the rotational axis,
    (b) obtaining a raw image, wherein the plurality of longitudinal markers are not visible in the raw image,
    (c) determining at least one of an apparent angular position of at least two of the plurality of longitudinal marker elements or a timing between signals from at least two of the plurality of longitudinal marker elements, and
    (d) computing a difference between a relative angular position and a theoretical angular position based on average rotational speed for the longitudinal marker elements.

19. The method of claim 18, further comprising displaying a message indicating the existence of NURD, the lack of NURD, or the amount of NURD.

20. The method of claim 18, wherein the step of computing the difference comprises:
 forming an estimation matrix based on the theoretical angular position of the longitudinal marker elements, and
 comparing a detected angular position of the longitudinal marker elements with the theoretical angular position of said longitudinal marker elements, and
 a step of correcting the raw image comprises resampling A-lines to a uniform spacing.

* * * * *